(12) United States Patent  
Becker et al.

(10) Patent No.: US 8,912,123 B2
(45) Date of Patent: Dec. 16, 2014

(54) SAFENED HERBICIDAL COMPOSITIONS INCLUDING 4-AMINO-3-CHLORO-5-FLUORO-6-(4-CHLORO-2-FLUORO-3-METHOXYPHENYL) PYRIDINE-2-CARBOXYLIC ACID OR A DERIVATIVE THEREOF AND METHODS FOR THEIR USE

(71) Applicants: Joerg Becker, Bad Aibling (DE); Thomas Schulz, Niederschoena (DE)

(72) Inventors: Joerg Becker, Bad Aibling (DE); Thomas Schulz, Niederschoena (DE)

(73) Assignee: Dow AgroSciences, LLC., Indianapolis, IN (US)

( * ) Notice: Subject to any disclaimer, the term of this patent is extended or adjusted under 35 U.S.C. 154(b) by 0 days.

(21) Appl. No.: 13/945,238

(22) Filed: Jul. 18, 2013

(65) Prior Publication Data

US 2014/0031225 A1     Jan. 30, 2014

Related U.S. Application Data

(60) Provisional application No. 61/674,990, filed on Jul. 24, 2012.

(51) Int. Cl.
*A01N 25/32*     (2006.01)
*A01N 43/40*     (2006.01)

(52) U.S. Cl.
CPC .............. *A01N 25/32* (2013.01); *A01N 43/40* (2013.01)
USPC ........................... 504/105; 504/130; 504/134

(58) Field of Classification Search
USPC .......................... 504/105, 128, 130, 134, 136
See application file for complete search history.

(56) References Cited

U.S. PATENT DOCUMENTS 7,314,849 B2 * 1/2008 Balko et al. .................. 504/244
2010/0137137 A1   6/2010 Rosinger et al.
2012/0115727 A1   5/2012 Satchivi et al.

FOREIGN PATENT DOCUMENTS

WO    WO03/011853 A1    2/2003
WO    WO2009/029518 A2  5/2009

OTHER PUBLICATIONS

PCT/US2013/051033 filed Jul. 18, 2013—International Search Report and Written Opinion citing the above-referenced applications.

* cited by examiner

*Primary Examiner* — Abigail Fisher
*Assistant Examiner* — Andriae M Holt
(74) *Attorney, Agent, or Firm* — Michael R. Asam

(57) ABSTRACT

A safened herbicidal composition for use, for example, in wheat or barley, comprising a herbicidally effective amount of (a) a compound of formula (I):

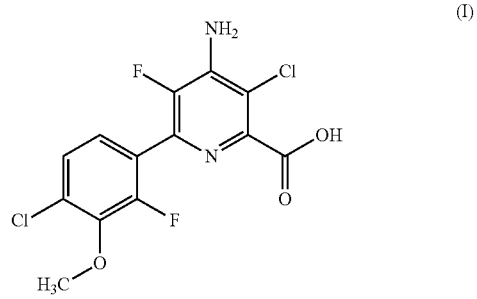

or an agriculturally acceptable salt or ester thereof and (b) a safener, for example, from the quinolinyloxyacetate family of chemicals, including, but not limited to, cloquintocet mexyl, provide weed control of undesirable vegetation.

19 Claims, No Drawings

SAFENED HERBICIDAL COMPOSITIONS INCLUDING 4-AMINO-3-CHLORO-5-FLUORO-6-(4-CHLORO-2-FLUORO-3-METHOXYPHENYL) PYRIDINE-2-CARBOXYLIC ACID OR A DERIVATIVE THEREOF AND METHODS FOR THEIR USE

This application claims the benefit of U.S. Provisional Patent Application Ser. No. 61/674,990, filed Jul. 24, 2012.

BACKGROUND

The protection of crops from weeds and other vegetation which inhibit crop growth is a constantly recurring problem in agriculture. To help combat this problem, researchers in the field of synthetic chemistry have produced an extensive variety of chemicals and chemical formulations effective in the control of such unwanted growth. Chemical herbicides of many types have been disclosed in the literature and a large number are in commercial use. Occasionally, however, such herbicides can injure the crop being protected in addition to the weeds and other vegetation intended to be controlled.

SUMMARY

Provided herein are safened herbicidal compositions comprising a herbicidally effective amount of (a) a compound of the formula (I)

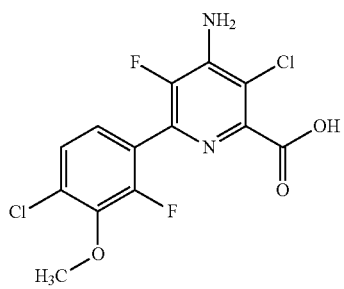

(I)

or an agriculturally acceptable salt or ester of thereof, and (b) a safener, e.g., from the quinolinyloxyacetate family of chemicals. The compositions may also contain an agriculturally acceptable adjuvant or carrier. The composition can be used, for example, in wheat or barley.

Provided herein also are methods of controlling undesirable vegetation comprising contacting the vegetation or applying to the soil or water to prevent the emergence or growth of vegetation a safened herbicidal composition comprising a herbicidally effective amount of (a) a compound of the formula (I)

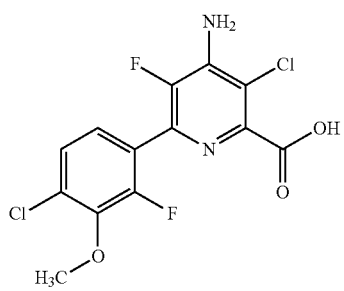

(I)

or an agriculturally acceptable salt or ester thereof and (b) a safener, e.g., from the quinolinyloxyacetate family of chemicals. The methods can be used, for example, in wheat or barley.

DETAILED DESCRIPTION

Definitions

As used herein, the compound of formula (I) has the following structure:

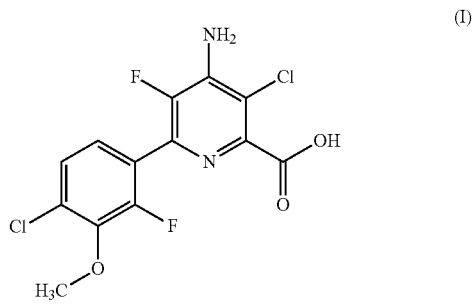 [SMILES: COc1c(Cl)ccc(-c2nc(C(=O)O)c(Cl)c(N)c2F)c1F]

(I)

The compound of formula (I) can be identified by the name 4-amino-3-chloro-6-(4-chloro-2-fluoro-3-methoxyphenyl)-5-fluoropyridine-2-carboxylic acid and has been described in U.S. Pat. No. 7,314,849 (B2), which is incorporated herein by reference in its entirety. Exemplary uses of the compound of the formula (I) include controlling undesirable vegetation, including grass, broadleaf and sedge weeds, in multiple non-crop and cropping situations.

As used herein, safeners from the quinolinyloxyacetate family of chemicals are described in U.S. Pat. No. 4,902,340. Safeners from the quinolinyloxyacetate family of chemicals include derivatives of cloquintocet, such as cloquintocet acid, cloquintocet mexyl, cloquintocet triisopropylamine, and cloquintocet dimethylamine. Cloquintocet is the common name for [(5-chloro-8-quinolinyl)oxy]acetic acid. Cloquintocet's safening activity is described in The Pesticide Manual, Fourteenth Edition, 2006.

As used herein, AD67 (MON 4660) is the common name for 4-(dichloroacetyl)-1-oxa-4-azaspiro-[4,5]decane. Its safening activity is described in The Pesticide Manual, Thirteenth Edition, 2003. AD67 (MON 4660) is known to be used as a safener in maize.

As used herein, beflubutamid is the common name for 2-[14-fluoro-3-(trifluoromethyl)phenoxyl-N-(phenylmethyl)butanamide. Its herbicidal activity is described in The Pesticide Manual, Fourteenth Edition, 2006. Beflubutamid is a compound under development, used either alone or in mixtures with isoproturon, for pre- and early post-emergence control of broadleaf weeds, such as *Veronica persica*, *Lamium amplexicaule* and *Viola arvensis*, in wheat and barley.

As used herein, benoxacor is the common name for 4-(dichloroacetyl)-3,4-dihydro-3-methyl-2H-1,4-benzoxazine. Its safening activity is described in Pesticide Outlook, 2001 (*The Royal Society of Chemistry*. [Online] 2001. pp. 10-15). Benoxacor is known to be used as a safener in maize.

As used herein, benthiocarb is the common name for S-[(4-chlorophenyl)methyl]N,N-diethylcarbamothioate. Its pesticide activity is described in PubChem Compound, 2005 (NCBI PubChem Compound, Benthiocarb-Compound Summary. http://pubchem.ncbi.nlm.nih.gov/summary/summary- .cgi?cid=34192# x281 (accessed July 2012). Benthiocarb is used to destroy unwanted vegetation, especially various types of weeds, grasses (POACEAE), and woody plants.

As used herein, bispyribac is the common name for 2,6-bis [(4,6-dimethoxy-2-pyrimidinyl)oxy]-benzoic acid. Its herbicidal activity is described in The Pesticide Manual, Fourteenth Edition, 2006. Bispyribac-sodium controls grasses, sedges and broadleaf weeds in direct-seeded rice.

As used herein, brassinolide is the common name for (1R, 3aS,3bS,6aS,8S,9R,10aR,10bS,12aS)-1-[(1S,2R,3R,4S)-2, 3-dihydroxy-1,4,5-trimethylhexyl]hexadecahydro-8,9-dihydroxy-10a,12a-dimethyl-6H-benz[c]indeno[5,4-e]oxepin-6-one. Its plant hormone activity is described in the Journal of Agronomy and Crop Science, 2011 (Anjum, S. A., et al. Brassinolide Application Improves the Drought Tolerance in Maize Through Modulation of Enzymatic Antioxidants and Leaf Gas Exchange. *Journal of Agronomy and Crop Science*, 197. 2011. pp. 177-185). Brassinolide is a naturally occurring substance, which modulates plant growth and development events and has been known to improve the crop tolerance to abiotic stresses.

As used herein, carfentrazone is the common name for .alpha.,2-dichloro-5-[4-(difluoromethyl)-4,5-dihydro-3-methyl-5-oxo-1H-1,-2,4-triazol-1-yl]-4-fluorobenzenepropanoic acid. Its herbicidal activity is described in The Pesticide Manual, Fourteenth Edition, 2006. Carfentrazone-ethyl controls a wide range of broadleaf weeds in cereals and rice.

As used herein, cyhalofop is the common name for (2R)-2-[4-(4-cyano-2-fluorophenoxy)phenoxy]-propanoic acid. Its herbicidal activity is described in The Pesticide Manual, Fourteenth Edition, 2006. Cyhalofop-butyl controls grass weeds in rice.

As used herein, cyometrinil is the common name for (αZ)-α-[(cyanomethoxy)imino]benzeneacetonitrile. Its safening activity is described in Pesticide Outlook, 2001 (*The Royal Society of Chemistry*. [Online] 2001. pp. 10-15). Cyometrinil is known to be used as a safener in sorghum.

As used herein, daimuron is the common name for N-(4-methylphenyl)-N'-(1-methyl-1-phenylethyl)-urea. Its herbicidal activity is described in The Pesticide Manual, Fourteenth Edition, 2006. Daimuron controls cyperaceous and annual grass weeds in paddy rice.

As used herein, dichlormid is the common name for N,N-diallyl-2,2-dichloroacetamide. Its safening activity is described in The Pesticide Manual, Fourteenth Edition, 2006. Dichlormid is known to be used as a safener for maize and sorghum.

As used herein, dicyclonon is the common name for 1-(dichloroacetyl)hexahydro-3,3,8a-trimethylpyrrolo[1,2-a]pyrimidin-6(2H)-one. Its safening activity is described in PubChem Compound, 2005 (NCBI PubChem Compound, Dicyclonon-Compound Summary. http://pubchem.ncbi.nlm.nih.gov/summary/summary.cgi?cid=115203 (accessed July 2012). Dicyclonon is known to be used as a safener in maize and cereal crops.

As used herein, dimepiperate is the common name for S-(1-methyl-1-phenylethyl)1-piperidine-carbothioate. Its herbicidal activity is described in The Pesticide Manual, Fourteenth Edition, 2006. Dimepiperate controls barnyardgrass (*Echinochloa crus-galli*) in paddy rice.

As used herein, disulfoton is the common name for O,O-diethyl S-[2-(ethylthio)ethyl]phosphorodithioate. Its insecticide activity is described in The Pesticide Manual, Fifteenth Edition, 2009. Disulfoton is used as an insecticide in potatoes, vegetables, sorghum, rice, tobacco, nut and other crops.

As used herein, fenchlorazole is the common name for 1-(2,4-dichlorophenyl)-5-(trichloromethyl)-1H-1,2,4-triazole-3-carboxylic acid. The ethyl ester fenchlorazole-ethyl can be used. Its safening activity is described in The Pesticide Manual, Fourteenth Edition, 2006. Fenchlorazole is known to be used as a safener in wheat, rye and triticale.

As used herein, fenclorim is the common name for 4,6-dichloro-2-phenylpyrimidine. Its safening activity is described in The Pesticide Manual, Fourteenth Edition, 2006. Fenclorim is known to be used as a safener in direct-seeded rice.

As used herein, flurazole is the common name for benzyl 2-chloro-4-trifluoromethylthiazole-5-carboxylate. Its safening activity is described in Pesticide Outlook, 2001 (*The Royal Society of Chemistry*. [Online] 2001. pp. 10-15). Flurazole is known to be used as a safener in sorghum.

As used herein, fluxofenim is the common name for 1-(4-chlorophenyl)-2,2,2-trifluoroethanone O-(1,3-dioxolan-2-ylmethyl)oxime. Its safening activity is described in The Pesticide Manual, Fourteenth Edition, 2006. Fluxofenim is known to be used as a safener in sorghum.

As used herein, furilazole is the common name for 3-(dichloroacetyl)-5-(2-furanyl)-2,2-dimethyl-oxazolidine. Its safening activity is described in The Pesticide Manual, Fourteenth Edition, 2006. Furilazole is known to be used as a safener in maize.

As used herein, halosulfuron is the common name for 3-chloro-5-[[[[(4,6-dimethoxy-2-pyrimidinyl)-amino]carbonyl]amino]sulfony-1]-1-methyl-1H-pyrazole-4-carboxylic acid. Its herbicidal activity is described in The Pesticide Manual, Fourteenth Edition, 2006. Halosulfuron-methyl controls annual broadleaf weeds and nutsedge in rice.

As used herein, harpin protein is a class of proteins produced in nature by certain bacterial plant pathogens. Its pesticide activity is described in Biopesticide Regulatory Action Document "Harpin Protein", 2002 (US Environmental Protection Agency Office of Pesticide Programs; Biopesticide Regulatory Action Document "Harpin Protein". [Online] 2002. pp 1-5). Harpin protein initiates a complex set of metabolic responses in the treated plant, causing natural gene expression and eliciting a plant's natural defense and growth systems.

As used herein, isoxadifen-ethyl is the common name for ethyl 4,5-dihydro-5,5-diphenyl-3-isoxazole-carboxylate. Its safening activity is described in The Pesticide Manual, Fourteenth Edition, 2006. Isoxadifen is known to be used as a safener in maize.

As used herein, jiecaowan is the common name for 2-(dichloromethyl)-2-methyl-1,3-dioxolane. Jiecaowan is known to be used as a safener.

As used herein, jiecaoxi is the common name for 2,2-dichloro-N-[2-oxo-2-(2-propen-1-ylamino)ethyl]-N-2-propen-1-ylacetamide. Jiecaoxi is known to be used as a safener.

As used herein, mefenpyr is the common name for 1-(2,4-dichlorophenyl)-4,5-dihydro-5-methyl-1H-pyrazole-3,5-dicarboxylic acid. Its safening activity is described in The Pesticide Manual, Fourteenth Edition, 2006. Mefenpyr is known to be used as a safener in wheat, rye, triticale and barley.

As used herein, mephenate is the common name for 4-chlorophenyl N-methylcarbamate. Mephanate is described at *ChemNet.*, Retrieved Jul. 18, 2012 from http://www.chemnet.com/. Mephanate is known to be used as a herbicide safener.

As used herein, naphthalic anhydride (NA) is the common name for 1H,3H-naphtho[1,8-cd]pyran-1,3-dione. Its safening activity is described in Pesticide Outlook, 2001 (*The Royal Society of Chemistry*. [Online] 2001. pp. 10-15). Naphthalic anhydride is known to be used as a safener in maize.

As used herein, norflurazon, is the common name for 4-chloro-5-(methylamino)-2-[3-(trifluoro-methyl)phenyl]-3 (2H)-pyridazinone. Its herbicidal activity is described in The Pesticide Manual, Fourteenth Edition, 2006. Norflurazon is used for the pre-emergence control of grasses and sedges, as well as some broadleaf weeds.

As used herein, oxabetrinil is the common name for (.alpha.Z)-.alpha.-[(1,3-dioxolan-2-yl)methoxyimino]-benzeneacetonitrile. Its safening activity is described in The Pesticide Manual, Fourteenth Edition, 2006. Oxabetrinil is known to be used as a safener in sorghum.

As used herein, pyriclor is the common name for 2,3,5-trichloro-4-pyridinol.

As used herein, R29148 is the common name for 2,2-dimethyl-6-methyldichloroacetyl oxazolidine. Its safening activity is described in The Pesticide Manual, Fifteenth Edition, 2009. R29148 is known to be used as a safener in maize.

As used herein, sulcotrione is the common name for 2-[2-chloro-4-(methylsulfonyl)benzoyl]-1,3-cyclohexanedione. Its herbicidal activity is described in The Pesticide Manual, Fourteenth Edition, 2006. Sulcotrione controls grass and broadleaf weeds.

As used herein, herbicide means an active ingredient that kills, controls or otherwise adversely modifies the growth of plants.

As used herein, a herbicidally effective or vegetation controlling amount is an amount of active ingredient which causes an adversely modifying effect and includes deviations from natural development, killing, regulation, desiccation, retardation, and the like.

As used herein, controlling undesirable vegetation means preventing, reducing, killing, or otherwise adversely modifying the development of plants and vegetation. Described herein are methods of controlling undesirable vegetation through the application of certain herbicide combinations or compositions. Methods of application include, but are not limited to applications to the vegetation or locus thereof, as well as preemergence, postemergence, and foliar applications.

As used herein, plants and vegetation include, but are not limited to, germinant seeds, emerging seedlings, plants emerging from vegetative propagules, and established vegetation.

As used herein, a safener is a compound that selectively protects crop plants from herbicide damage without significantly reducing activity in target weed species.

As used herein, agriculturally acceptable salts and esters refer to salts and esters that exhibit herbicidal activity, or that are or can be converted in plants, water, or soil to the referenced herbicide. Exemplary agriculturally acceptable esters are those that are or can by hydrolyzed, oxidized, metabolized, or otherwise converted, e.g., in plants, water, or soil, to the corresponding carboxylic acid which, depending on the pH, may be in the dissociated or undissociated form. Exemplary salts include those derived from alkali or alkaline earth metals and those derived from ammonia and amines. Exemplary cations include sodium, potassium, magnesium, and aminium cations of the formula:

$$R^1R^2R^3R^4N^+$$

wherein $R^1$, $R^2$, $R^3$ and $R^4$ each, independently represents hydrogen or $C_1$-$C_{12}$ alkyl, $C_3$-$C_{12}$ alkenyl or $C_3$-$C_{12}$ alkynyl, each of which is optionally substituted by one or more hydroxy, $C_1$-$C_4$ alkoxy, $C_1$-$C_4$ alkylthio or phenyl groups, provided that $R^1$, $R^2$, $R^3$ and $R^4$ are sterically compatible. Additionally, any two of $R^1$, $R^2$, $R^3$ and $R^4$ together may represent an aliphatic difunctional moiety containing one to twelve carbon atoms and up to two oxygen or sulfur atoms. Salts can be prepared by treatment with a metal hydroxide, such as sodium hydroxide, with an amine, such as ammonia, trimethylamine, diethanolamine, 2-methylthiopropylamine, bisallylamine, 2-butoxyethylamine, morpholine, cyclododecylamine, or benzylamine or with a tetraalkylammonium hydroxide, such as tetramethylammonium hydroxide or choline hydroxide.

Exemplary esters include those derived from $C_1$-$C_{12}$ alkyl, $C_3$-$C_{12}$ alkenyl, $C_3$-$C_{12}$ alkynyl or $C_7$-$C_{10}$ aryl-substituted alkyl alcohols, such as methyl alcohol, isopropyl alcohol, 1-butanol, 2-ethylhexanol, butoxyethanol, methoxypropanol, allyl alcohol, propargyl alcohol, cyclohexanol or unsubstituted or substituted benzyl alcohols. Benzyl alcohols may be substituted with from 1-3 substituents independently selected from halogen, $C_1$-$C_4$ alkyl or $C_1$-$C_4$ alkoxy. Esters can be prepared by coupling of the acids with the alcohol using any number of suitable activating agents such as those used for peptide couplings such as dicyclohexylcarbodiimide (DCC) or carbonyl diimidazole (CDI); by reacting the acids with alkylating agents such as alkylhalides or alkylsulfonates in the presence of a base such as triethylamine or lithium carbonate; by reacting the corresponding acid chloride of an acid with an appropriate alcohol; by reacting the corresponding acid with an appropriate alcohol in the presence of an acid catalyst or by transesterification.

Compositions and Methods

Provided herein are safened herbicidal compositions, for example in wheat or barley, comprising a herbicidally effective amount of (a) a compound of the formula (I)

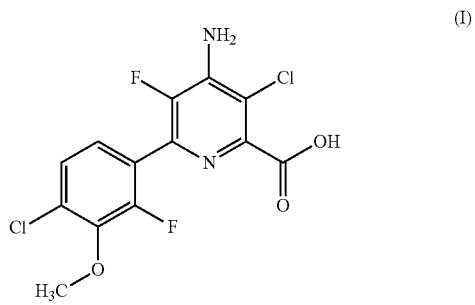 [SMILES: COc1c(Cl)ccc(-c2nc(C(=O)O)c(Cl)c(N)c2F)c1F]

or an agriculturally acceptable salt or ester of thereof, and (b) a safener, e.g., from the quinolinyloxyacetate family of chemicals, including but not limited to, cloquintocet acid, cloquintocet mexyl, cloquintocet triisopropylamine, or cloquintocet dimethylamine.

Provided herein are also methods of controlling undesirable vegetation, for example in wheat or barley, comprising contacting the vegetation or applying to the soil or water adjacent thereto with a safened herbicidal composition including a herbicidally effective amount of (a) the compound of formula (I) or an agriculturally acceptable salt or ester thereof and (b) a safener, e.g., from the quinolinyloxyacetate family of chemicals, including, but not limited to, cloquintocet acid, cloquintocet mexyl, cloquintocet triisopropylamine, or cloquintocet dimethylamine.

Crops, including, for example, wheat and/or barley, to be protected from the adverse effect of undesirable plant growth may be damaged to a certain degree when an effective dose of herbicide is used. Safening means preventing the adverse effect of a herbicide on the crop, i.e., protecting the crop without, at the same time, noticeably influencing the herbicidal action on the undesirable plant growth, i.e., weeds, to be combated.

Compounds that have known safening effect and can be used as safeners with the safened compositions described herein in certain crops include, but are not limited to, compounds such as AD-67 (MON 4660), beflubutamid, benoxacor, benthiocarb, bispyribac, brassinolide, carfentrazone, cyhalofop, cyometrinil, daimuron, dichlormid, dicyclonon, dimepiperate, disulfoton, fenchlorazole, fenclorim, flurazole, fluxofenim, furilazole, halosulfuron, harpin proteins, isoxadifen, jiecaowan, jiecaoxi, mefenpyr, mephenate, naphthalic anhydride (NA), norflurazon, oxabetrinil, pyriclor, R29148, sulcotrione, and N-phenyl-sulfonylbenzoic acid amides, to enhance their selectivity.

The compound of the formula (I) or an agriculturally acceptable salt or ester of thereof, and (b) a safener, e.g., from the quinolinyloxyacetate family of chemicals described herein can be applied either separately or together as part of a system. When part of a system, for example, the compound of the formula (I) or an agriculturally acceptable salt or ester of thereof, and (b) a safener, e.g., from the quinolinyloxyacetate family of chemicals described herein can be formulated in one composition, tank mixed, applied simultaneously, or applied sequentially.

Herbicidal activity is exhibited by the compounds of formula (I) when they are applied directly to a plant or to the area adjacent the plant at any stage of growth. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted to promote non-selective or selective herbicidal action. The compositions of formula (I) described herein can be applied as a post-emergence application, or pre-emergence application, to relatively immature undesirable vegetation to achieve the maximum control of weeds.

The compositions and methods provided herein can be used to control weeds in crops, including but not limited to cereal crops, direct-seeded, water-seeded and transplanted rice, wheat, durum, barley, oats, rye, sorghum, triticale, corn/maize, soybean, cotton, canola, oilseed rape, pastures, grasslands, rangelands, fallowland, turf, tree and vine orchards, aquatics, and IVM, and also in glyphosate, glufosinate, dicamba, imidazolinone, phenoxy auxin, pyridyloxy auxin, aryloxyphenoxypropionate, acetyl CoA carboxylase (ACCase), acetolactate synthase (ALS), 4-hydroxyphenyl-pyruvate dioxygenase (HPPD, protoporphyrinogen oxidase (PPO), triazine, and bromoxynil tolerant crops (such as, but not limited to, soybean, cotton, canola/oilseed rape, rice, cereals, corn, turf, wheat, barley, etc).

The compositions and methods provided herein can be used to control undesirable vegetation consisting, for example, of grass, broadleaf and sedge weeds. For example, the compositions and methods provided herein can be used to control undesirable vegetation including, but not limited to, undesirable vegetation of the weed genera *Helianthus, Heteranthera, Jacquemontia, Kochia, Lactuca, Lamium, Matricaria, Monochoria, Papaver, Plantago, Sagittaria, Sesbania, Sida, Sinapis, Sphenoclea, Stellaria, Taraxacum,* and *Xanthium.* Examples of grass weeds controlled by the compositions and methods provided herein include, but are not limited to, *Brachiaria platyphylla* (Broadleaf signalgrass, BRAPP), *Echinochloa crus-galli* (Barnyardgrass, ECHCG), *Echinochloa colonum* (Junglerice, ECHCO), *Echinochloa oryzoides* (Early watergrass, ECHOR), *Leptochloa chinensis* (Chinese sprangletop, LEFCH), *Leptochloa fascicularis* (Bearded sprangletop, LEFFA), *Leptochloa panicoides* (Amazon sprangletop, LEFPA), *Ischaemum rugosum Salisb.* (Poaceae saramollagrass, ISCRU ISRU), and *Setaria faberi* (Giant foxtail, SETFA). Examples of sedge weeds controlled by the compositions and methods provided herein include, but are not limited to, *Cyperus difformis* (Smallflower flatsedge, CYPDI), *Cyperus esculentus* (Yellow nutsedge, CYPES), *Cyperus iria* (Rice flatsedge, CYPIR), *Cyperus rotundus* (Purple nutsedge, CYPRO), *Fimbristylis miliacea* (Globe fringerush, FIMMI), *Scirpus juncoides* (Smallflower flatsedge, SCPJU), and *Scirpus mucronatus* (Ricefield bulrush, SCPMU). Examples of broadleaf weeds controlled by the compositions and methods provided herein include, but are not limited to, *Abutilon theophrasti* (Velvetleaf, ABUTH), *Aeschynomene* species (Jointvetch, AESSS), *Alternanthera philoxeroides* (Alligatorweed, ALRPH), *Alisma plantago-aquatica* (Common waterplantain, ALSPA), *Amaranthus blitoides* (Prostrate pigweed, AMABL), *Amaranthus palmeri* (Palmer amaranth, AMAPA), *Amaranthus retroflexus* (Redroot pigweed, AMARE), *Amaranthus tamariscinus* (Common waterhemp, AMATA), *Amaranthus tuberculatos* (Tall waterhemp, AMATU), *Ambrosia elatior* (Common ragweed, AMBEL), *Ambrosia psilostachya* (Western ragweed, AMBPS), *Ambrosia trifida* (Giant ragweed, AMBTR), *Ammannia coccinea* (Purple ammannia, AMMCO), *Chenopodium album* (Common lambsquarters, CHEAL), *Cirsium arvense* (Canada thistle, CIRAR), *Commelina benghalensis* (Tropical spiderwort, COMBE), *Daucus carota* (Wild carrot, DAUCA), *Eclipta alba* (American false daisy, ECLAL), *Euphorbia heterophylla* (Wild poinsettia, EPHHL), *Erigeron bonariensis* (Hairy fleabane, ERIBO), *Erigeron canadensis* (Canadian fleabane, ERICA), *Fumaria officinalis* (Common fumitory, FUMOF), *Galium aparine* (Catchweed bedstraw, GALAP), *Geranium dissectum* (Cutleaf geranium, GERDI), *Helianthus annuus* (Common sunflower, HELAN), *Heteranthera limosa* (Ducksalad, HETLI), *Jacquemontia tamnifolia* (Smallflower morningglory, IAQTA), *Ipomoea lacunose* (White morningglory, IPOLA), *Kochia scoparia,* (Kochia, KCHSC), *Lactuca serriola* (Prickly lettuce, LACSE), *Lamium purpureum* (Purple deadnettle, LAMPU), *Matricaria chamomilla* (Wild chamomile, MATCH), *Monochoria vaginalis* (Monochoria, MOOVA), *Papaver rhoeas* (Field poppy, PAPRH), *Plantago lanceolata* (Buckhornn plantain, PLALA), *Sagittaria species* (Arrowhead, SAGSS), *Sesbania exaltata* (Hemp sesbania, SEBEX), *Sida spinosa* (Prickly sida, SIDSP), *Sinapis arvensis* (Wild mustard, SINAR), *Sphenoclea zeylanica* (Gooseweed, SPDZE), *Stellaria media* (Common chickweed, STEME), *Taraxacum officinale* (Commonn dandelion, TAROF), and *Xanthium strumarium* (Common cocklebur, XANST). Additional examples of weeds controlled by the compositions and methods provided herein include, but are not limited to *Echinochloa oryzicola* (Vasinger) Vasinger ECHPH Poaceae watergrass, late; *Lindernia dubia* (L.) Pennell LIDDU Scrophulariaceae falsepimpernel, low; *Heteranthera reniformis* R. & P. HETRE Pontederiaceae mudplantain, roundleaf; *Murdannia nudiflora* (L.) Brenan MUDNU MUNU Commelinaceae doveweed; *Alternanthera philoxeroides* (Mart.) Griseb. ALRPH ALPH Amaranthaceae alligatorweed; MOOKO; and *Schoenoplectus maritimus* SCPMA. Additionally, the compositions and methods provided herein can be used to control undesirable vegetation including *Apera spica venti* (loose silky-bent, APESV). For further example, the combination of (a) compound (I) or agriculturally acceptable ester or salt thereof and (b) a safener, e.g., from the quinolinyloxyacetate family of chemicals, including but not limited to, cloquintocet acid, cloquintocet mexyl, cloquintocet triisopropylamine, or cloquintocet dimethylamine is used to control *Apera spica venti* (loose silky-bent, APESV).

In the compounds and methods described herein, an agriculturally acceptable ester or salt of compound (I) is employed. An agriculturally acceptable ester, such as an aralkyl or alkyl ester, can be employed. The ester can be a $C_{1-4}$ alkyl ester, a n-butyl ester, a benzyl ester, or a substituted benzyl ester. Additionally, the carboxylic acid form of compound (I) or the carboxylate salt of the compound of formula (I) can be used.

In the compositions and methods described herein, the compound of formula (I) or salt or ester thereof is used in combination with a safener, e.g., from the quinolinyloxyacetate family of chemicals. The weight ratio of the compound of formula (I) or salt or ester thereof to the safener, e.g., from the quinolinyloxyacetate family of chemicals, is within the range of from 64:1 to 1:32. The weight ratio of the compound of formula (I) or salt or ester thereof to the safener, e.g., from the quinolinyloxyacetate family of chemicals, also can be within the range from 48:1 to 1:32, 36:1 to 1:32, 32:1 to 1:32, 28:1 to 1:32, 24:1 to 1:32, 20:1 to 1:32, 18:1 to 1:32, 16:1 to 1:32, 14:1 to 1:32, 12:1 to 1:32, 10:1 to 1:32, 8:1 to 1:32, 6:1 to 1:32, 4:1 to 1:32, 3:1 to 1:32, 2:1 to 1:32, 1:1 to 1:32, 1:1 to 1:28, 1:1 to 1:24, 1:1 to 1:20, 1:1 to 1:18, 1:1 to 1:16, 1:1 to 1:14, 1:1 to 1:12, 1:1 to 1:10, 1:1 to 1:8, 1:1 to 1:6, 1:1 to 1:4, 1:1 to 1:2, 36:1 to 1:28, 32:1 to 1:24, 28:1 to 1:20, 24:1 to 1:20, 20:1 to 1:20, 18:1 to 1:18, 16:1 to 1:16, 14:1 to 1:14, 12:1 to 1:12, 10:1 to 1:10, 8:1 to 1:8, 6:1 to 1:6, 4:1 to 1:4, or 2:1 to 1:2. Additionally, the weight ratio of the compound of formula (I) or salt or ester thereof to the safener, e.g., from the quinolinyloxyacetate family of chemicals, can be 1:1, 1.1:1, 1.2:1, 1.3:1, 1.4:1, 1.5:1, 1.6:1, 1.7:1, 1.8:1, 1.9:1, 2:1, 2.5:1, 3:1, 4:1, 5:1, 6:1, 7:1, 8:1, 9:1, 10:1, 11:1, 12:1, 14:1, 16:1, 18:1, 20:1, 24:1, 28:1, 32:1, 48:1, 1:1.1, 1:1.1, 1:1.3, 1:1.4, 1:1.5, 1:1.6, 1:1.7, 1:1.8, 1:1.9, 1:2, 1:2.5, 1:3, 1:4, 1:5, 1:6, 1:7, 1:8, 1:9, 1:10, 1:11, 1:12, 1:14, 1:16, 1:18, 1:20, 1:24, 1:28, 1:32, or 1:48.

The application rate will depend upon the particular type of weed to be controlled, the degree of control required, and the timing and method of application. In the compositions described herein the compound of formula (I) or salt or ester thereof can be applied at an application rate of from 1 grams active ingredient per hectare (g ai/ha) to 300 g ai/ha based on the total amount of the compound of formula (I) or salt or ester thereof in the composition. Additionally, in the compositions described herein the compound of formula (I) or salt or ester thereof can be applied at an application rate of from 1 g ai/ha to 250 g ai/ha, 2 g ai/ha to 250 g ai/ha, 5 g ai/ha to 250 g ai/ha, 1 g ai/ha to 200 g ai/ha, 2 g ai/ha to 200 g ai/ha, 5 g ai/ha to 200 g ai/ha, 12.5 g ai/ha to 250 g ai/ha, 12.5 g ai/ha to 200 g ai/ha, 1 g ai/ha to 150 g ai/ha, 1 g ai/ha to 100 g ai/ha, 1 g ai/ha to 75 g ai/ha, 1 g ai/ha to 50 g ai/ha, 2 g ai/ha to 50 g ai/ha, or 5 g ai/ha to 50 g ai/ha based on the total amount of the compound of formula (I) or salt or ester thereof in the composition. In the compositions described herein the safener or a compatible herbicide capable of safening can be applied at an application rate of from 1 g ai/ha to 1200 g ai/ha. Additionally, in the compositions described herein the safener or a compatible herbicide capable of safening can be applied at an application rate of from 1 g ai/ha to 600 g ai/ha, 1 g ai/ha to 500 g ai/ha, 1 g ai/ha to 400 g ai/ha, 1 g ai/ha to 300 g ai/ha, 1 g ai/ha to 200 g ai/ha, 1 g ai/ha to 100 g ai/ha, 4 g ai/ha to 1200 g ai/ha, 4 g ai/ha to 600 g ai/ha, 50 g ai/ha to 600 g ai/ha, 50 g ai/ha to 500 g ai/ha, 50 g ai/ha to 400 g ai/ha, 50 g ai/ha to 300 g ai/ha, 50 g ai/ha to 200 g ai/ha, 50 g ai/ha to 150 g ai/ha, 50 g ai/ha to 100 g ai/ha, 100 g ai/ha to 1200 g ai/ha, 100 g ai/ha to 600 g ai/ha, 100 g ai/ha to 500 g ai/ha, 100 g ai/ha to 400 g ai/ha, 100 g ai/ha to 300 g ai/ha, or 100 g ai/ha to 200 g ai/ha based on the total amount of the safener or a compatible herbicide capable of safening in the composition. For example, a safener from the quinolinyloxyacetate family of chemicals can be applied at a rate from 0.273 g ai/ha to 70 g ai/ha and the compound of formula (I) of salt or ester thereof is applied at a rate from 1 g ae/ha to 300 g ae/ha.

The components of the mixtures described herein can be applied either separately or as part of a multipart herbicidal system.

The safened herbicide mixtures described herein can be applied in conjunction with one or more other herbicides to control a wider variety of undesirable vegetation. When used in conjunction with other herbicides, the composition can be formulated with the other herbicide or herbicides, tank mixed with the other herbicide or herbicides or applied sequentially with the other herbicide or herbicides. Some of the herbicides that can be employed in conjunction with the compositions and methods described herein include, but are not limited to: 4-CPA; 4-CPB; 4-CPP; 2,4-D; 2,4-D choline salt, 2,4-D esters and amines, 2,4-DB; 3,4-DA; 3,4-DB; 2,4-DEB; 2,4-DEP; 3,4-DP; 2,3,6-TBA; 2,4,5-T; 2,4,5-TB; acetochlor, acifluorfen, aclonifen, acrolein, alachlor, allidochlor, alloxydim, allyl alcohol, alorac, ametridione, ametryn, amibuzin, amicarbazone, amidosulfuron, aminocyclopyrachlor, aminopyralid, amiprofos-methyl, amitrole, ammonium sulfamate, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron-methyl, bensulide, benthiocarb, bentazon-sodium, benzadox, benzfendizone, benzipram, benzobicyclon, benzofenap, benzofluor, benzoylprop, benzthiazuron, bicyclopyrone, bifenox, bilanafos, bispyribac-sodium, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole chlorprocarb, carfentrazone-ethyl, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlornitrofen, chloropon, chlorotoluron, chloroxuron, chloroxynil, chlorpropham, chlorsulfuron, chlorthal, chlorthiamid, cinidon-ethyl, cinmethylin, cinosulfuron, cisanilide, clethodim, cliodinate, clodinafop-propargyl, clofop, clomazone, clomeprop, cloprop, cloproxydim, clopyralid, cloransulam-methyl, CMA, copper sulfate, CPMF, CPPC, credazine, cresol, cumyluron, cyanatryn, cyanazine, cycloate, cyclosulfamuron, cycloxydim, cycluron, cyhalofop-butyl, cyperquat, cyprazine, cyprazole, cypromid, daimuron, dalapon, dazomet, delachlor, desmedipham, desmetryn, di-allate, dicamba, dichlobenil, dichloralurea, dichlormate, dichlorprop, dichlorprop-P, diclofop-methyl, diclosulam, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethbenzamide, ethametsulfuron, ethidimuron, ethiolate, ethobenzamid, etobenzamid, ethofumesate, ethoxyfen, ethoxysulfuron, etinofen, etnipromid, etobenzanid, EXD, fenasulam, fenoprop, fenoxaprop, fenoxaprop-P-ethyl, fenoxaprop-P-ethyl+ isoxadifen-ethyl, fenoxasulfone, fenteracol, fenthiaprop, fentrazamide, fenuron, ferrous sulfate, flamprop, flamprop-M, flazasulfuron, florasulam, fluazifop, fluazifop-P-butyl, fluazolate, flucarbazone, flucetosulfuron, fluchloralin, flufenacet, flufenican, flufenpyr-ethyl, flumetsulam, flumezin, flumiclorac-pentyl, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, flurochloridone, fluroxypyr, flurtamone, fluthiacet, fomesafen, foramsulfuron, fosamine, fumiclorac, furyloxyfen, glufosinate, glufosinate-ammonium, glufosinate-P-ammonium, glyphosate, halosafen, halosulfuron-methyl, haloxydine, haloxyfop-methyl, haloxyfop-P-methyl, hexachloroacetone, hexaflurate, hexazinone, imazamethabenz, imazamox, imazapic, imazapyr, imazaquin, imazosulfuron, imazethapyr, indanofan, indaziflam, iodobonil, iodomethane, iodosulfuron, iodosulfuron-ethyl-sodium, iofensulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA esters and amines, MCPA-thioethyl, MCPB, mecoprop, mecoprop-P, medinoterb, mefenacet, mefluidide, mesoprazine, mesosulfuron, mesotrione, metam, metamifop, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, metsulfuron, metsulfuron-methyl, molinate, monalide, monisouron, monochloroacetic acid, monolinuron, monuron, morfamquat, MSMA, naproanilide, napropamide, naptalam, neburon, nicosulfuron, nipyraclofen, nitralin, nitrofen, nitrofluorfen, norflurazon, noruron, OCH, orbencarb, orthodichlorobenzene, orthosulfamuron, oryzalin, oxadiargyl, oxadiazon, oxapyrazon, oxasulfuron, oxaziclomefone, oxyfluorfen, paraflufen-ethyl, parafluron, paraquat, pebulate, pelargonic acid, pendimethalin, penoxsulam, pentachlorophenol, pentanochlor, pentoxazone, perfluidone, pethoxamid, phenisopham, phenmedipham, phenmedipham-ethyl, phenobenzuron, phenylmercury acetate, picloram, picolinafen, pinoxaden, piperophos, potassium arsenite, potassium azide, potassium cyanate, pretilachlor, primisulfuron-methyl, procyazine, prodiamine, profluazol, profluralin, profoxydim, proglinazine, prohexadione-calcium, prometon, prometryn, pronamide, propachlor, propanil, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen-ethyl, pyrasulfotole, pyrazogyl, pyrazolynate, pyrazosulfuron-ethyl, pyrazoxyfen, pyribenzoxim, pyributicarb, pyriclor, pyridafol, pyridate, pyriftalid, pyriminobac, pyrimisulfan, pyrithiobac-sodium, pyroxasulfone, pyroxsulam, quinclorac, quinmerac, quinoclamine, quinonamid, quizalofop, quizalofop-P-ethyl, rhodethanil, rimsulfuron, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfometuron, sulfosate, sulfosulfuron, sulfuric acid, sulglycapin, swep, TCA, tebutam, tebuthiuron, tefuryltrione, tembotrione, tepraloxydim, terbacil, terbucarb, terbuchlor, terbumeton, terbuthylazine, terbutryn, tetrafluron, thenylchlor, thiazafluron, thiazopyr, thidiazimin, thidiazuron, thiencarbazone-methyl, thifensulfuron, thifensulfurn-methyl, thiobencarb, tiocarbazil, tioclorim, topramezone, tralkoxydim, triafamone, tri-allate, triasulfuron, triaziflam, tribenuron, tribenuron-methyl, tricamba, triclopyr choline salt, triclopyr esters and salts, tridiphane, trietazine, trifloxysulfuron, trifluralin, triflusulfuron, trifop, trifopsime, trihydroxytriazine, trimeturon, tripropindan, tritac tritosulfuron, vernolate, xylachlor and salts, esters, optically active isomers and mixtures thereof.

The safened compositions and methods for their use described herein, can, further, be used in conjunction with glyphosate, glufosinate, dicamba, phenoxy auxins, pyridyloxy auxins, aryloxyphenoxypropionates, acetyl CoA carboxylase (ACCase) inhibitors, imidazolinones, acetolactate synthase (ALS) inhibitors, 4-hydroxyphenyl-pyruvate dioxygenase (HPPD) inhibitors, protoporphyrinogen oxidase (PPO) inhibitors, triazines, and bromoxynil on glyphosate-tolerant, glufosinate-tolerant, dicamba-tolerant, phenoxy auxin-tolerant, pyridyloxy auxin-tolerant, aryloxyphenoxypropionate-tolerant, ACCase-tolerant, imidazolinone-tolerant, ALS-tolerant, HPPD-tolerant, PPO-tolerant, triazine-tolerant, bromoxynil-tolerant, and crops possessing multiple or stacked traits conferring tolerance to multiple chemistries and/or multiple modes of action. The compound of formula (I) or salt or ester thereof and complementary herbicide or salt or ester thereof can be used in combination with herbicides that are selective for the crop being treated and which complement the spectrum of weeds controlled by these compounds at the application rate employed. The compositions described herein and other complementary herbicides can be applied at the same time, either as a combination formulation or as a tank mix.

The safened compositions described herein can also include with one or more additional herbicide safeners, such as AD-67 (MON 4660), benoxacor, benthiocarb, brassinolide, cloquintocet (mexyl), cyometrinil, daimuron, dichlormid, dicyclonon, dimepiperate, disulfoton, fenchlorazole-ethyl, fenclorim, flurazole, fluxofenim, furilazole, harpin proteins, isoxadifen-ethyl, jiecaowan, jiecaoxi, mefenpyr-diethyl, mephenate, naphthalic anhydride (NA), oxabetrinil, R29148 and N-phenyl-sulfonylbenzoic acid amides, to enhance their selectivity.

The compositions provided herein can further include one or more agriculturally acceptable adjuvant or carrier. Suitable adjuvants or carriers should not be phytotoxic to valuable crops, particularly at the concentrations employed in applying the compositions for selective weed control in the presence of crops, and should not react chemically with herbicidal components or other composition ingredients. Such mixtures can be designed for application directly to weeds or their locus or can be concentrates or formulations that are normally diluted with additional carriers and adjuvants before application. The adjuvants or carriers can be solids, such as, for example, dusts, granules, water-dispersible granules, or wettable powders, or liquids, such as, for example, emulsifiable concentrates, solutions, emulsions or suspensions. Additionally, the adjuvants or carriers can also be provided as a pre-mix or tank mixed.

Suitable agricultural adjuvants and carriers are well known to those of skill in the art and include, but are not limited to, crop oil concentrate; nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate;

emulsified methylated seed oil; tridecyl alcohol (synthetic) ethoxylate (8EO); tallow amine ethoxylate (15 EO); PEG (400) dioleate-99.

Examples of liquid carriers that can be used in the compositions and methods described herein include water and organic solvents. Examples of useful organic solvents include, but are not limited to, petroleum fractions or hydrocarbons such as mineral oil, aromatic solvents, paraffinic oils, and the like; vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like; esters of the above vegetable oils; esters of monoalcohols or dihydric, trihydric, or other lower polyalcohols (4-6 hydroxy containing), such as 2-ethyl hexyl stearate, n-butyl oleate, isopropyl myristate, propylene glycol dioleate, di-octyl succinate, di-butyl adipate, di-octyl phthalate and the like; esters of mono, di and polycarboxylic acids and the like. Specific organic solvents include, but are not limited to toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers and the like. Water is useful as a carrier for the dilution of concentrates.

Suitable solid carriers include but are not limited to talc, pyrophyllite clay, silica, attapulgus clay, kaolin clay, kieselguhr, chalk, diatomaceous earth, lime, calcium carbonate, bentonite clay, Fuller's earth, cottonseed hulls, wheat flour, soybean flour, pumice, wood flour, walnut shell flour, lignin, cellulose, and the like.

The compositions described herein may further include one or more surface-active agents. Such surface-active agents can be used in both solid and liquid compositions, and can be designed to be diluted with carrier before application. The surface-active agents can be anionic, cationic or nonionic in character and can be employed as emulsifying agents, wetting agents, suspending agents, or for other purposes. Surfactants which may also be used in the present formulations are described, inter alia, in "McCutcheon's Detergents and Emulsifiers Annual," MC Publishing Corp., Ridgewood, N.J., 1998 and in "Encyclopedia of Surfactants," Vol. I-III, Chemical Publishing Co., New York, 1980-81. Surface-active agents include, but are not limited to salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalene-sulfonate salts, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono and dialkyl phosphate esters; vegetable or seed oils such as soybean oil, rapeseed/canola oil, olive oil, castor oil, sunflower seed oil, coconut oil, corn oil, cottonseed oil, linseed oil, palm oil, peanut oil, safflower oil, sesame oil, tung oil and the like; and esters of the above vegetable oils, e.g., methyl esters. These materials, such as vegetable or seed oils and their esters, can be used interchangeably as an agricultural adjuvant, as a liquid carrier or as a surface active agent.

Other additives useful in the compositions provided herein include, but are not limited to, compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulants, fungicides, insecticides, and the like and can be formulated with liquid fertilizers or solid, particulate fertilizer carriers such as ammonium nitrate, urea and the like.

The concentration of active ingredients in the compositions described herein is generally from 0.0005 to 98 percent by weight. Additionally, concentration is from 0.0006 to 90 percent by weight can be used. In compositions designed to be employed as concentrates, the active ingredients, can be present in a concentration from 0.1 to 98 weight percent, or from 0.5 to 90 weight percent. Such compositions can be diluted with an inert carrier, such as, for example, water, before application. The diluted compositions usually applied to vegetation or the soil or water adjacent thereto can contain from 0.0006 to 15.0 weight percent active ingredient or from 0.001 to 10.0 weight percent.

The present compositions can be applied to vegetation or the soil or water adjacent thereto by the use of conventional ground or aerial dusters, sprayers, and granule applicators, by addition to irrigation or paddy water, and by other conventional means known to those skilled in the art.

The described compositions and methods and following examples are for illustrative purposes and are not intended to limit the scope of the claims. Other modifications, uses, or combinations with respect to the compositions and methods described herein will be apparent to a person of ordinary skill in the art without departing from the spirit and scope of the claimed subject matter.

EXAMPLE

Evaluation of Postemergence Herbicidal Activity

A post-emergence field trial was conducted under field conditions in Helbigsdorf, Germany. Trial site was located in commercially grown fields of winter barley (*Hordeum vulgare*, HORVW) using standard herbicide small plot research methodology. Postemergence trial plot was 2.5 meter (m)×5 m (width×length) with 3 replicates per treatment. The crop was grown using normal cultural practices for fertilization, seeding, and maintenance to ensure good growth of the crop and the weeds.

Trial treatments included spray formulations containing 4-amino-3-chloro-5-fluoro-6-(4-chloro-2-fluoro-3-methoxy-phenyl)pyridine-2-carboxylic acid (Compound A) at various rates and optionally including cloquintocet mexyl. All treatments in the post-emergence field trials were applied using a bicycle sprayer compressed air/gas sprayer with flat fan nozzles (90°) calibrated to apply 200 L/ha spray volume at approximately 250 kPa nozzle pressure. The spray formulations for Trials 1-4 listed in Table 1 included Dow AgroSciences testing formulation Compound A (listed in acid equivalent per hectare (g ae/ha)), Agnique BL3095 (Cognis, France; listed as liters of product per hectare (L pr/ha)), and optionally cloquintocet mexyl (listed as grams of active ingredient per hectare (g ai/ha)). The spray solutions were mixed in water at the levels indicated in Table 1 to achieve the desired rates based on a unit area of application (hectare). Data for observed visual injury is provided for 227 days after application (DAA) in Table 1. Visual crop injury (ear deformation) was scored on a scale of 0 to 100 percent where 0 corresponds to no injury and 100 correspond to damage at all plants.

All treatment results, both for the single product and mixture, are with 4 replicates. The trial sites had naturally occurring populations of weeds. The weed spectrum included loose silky-bent (*Apera spica-venti*, APESV).

TABLE 1

Safening Results

| Trial # | Compound A[a] g ae/ha | Cloquintocet-mexyl safener g ai/ha | Observed Visual Injury - Ear Deformation (%) 227 DAA HORVW |
|---|---|---|---|
| 1 | 10 | | 27 |
| 2 | 20 | | 30 |
| 3 | 30 | | 30 |
| 4 | 30 | 18.75 | 0 |

[a]Including one liter of Agnique BL3095 per hectare.
HORVW = winter barley (*Hordeum vulgare*)

As can be readily seen from the results shown in Table 1, cloquintocet-mexyl safened the compound of formula I in winter barley.

What is claimed is:

1. A safened herbicidal composition comprising a herbicidally effective amount of (a) the benzyl ester of the compound of formula (I)

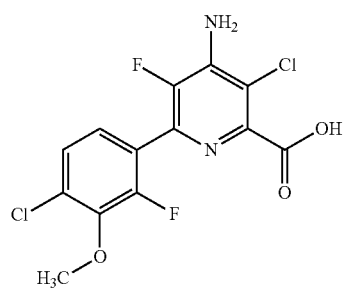

and (b) a safener.

2. The composition of claim 1, wherein the safened herbicidal composition is for use in wheat or barley.

3. The composition of claim 1, wherein the safener is from the quinolinyloxyacetate family of chemicals.

4. The composition of claim 3, wherein the safener is cloquintocet acid, cloquintocet mexyl, cloquintocet triisopropylamine, or cloquintocet dimethylamine.

5. The composition of claim 4, wherein the safener is cloquintocet mexyl.

6. The composition of claim 1, wherein (a) is an agriculturally acceptable benzyl ester of the compound of formula (I) and (b) is cloquintocet mexyl.

7. The composition of claim 1, wherein the weight ratio (a) to (b) is from 64:1 to 1:32.

8. The composition of claim 1, wherein the weight ratio of (a) to (b) is from 2:1 to 1:2.

9. The composition of claim 1, further comprising an agriculturally acceptable adjuvant or carrier.

10. A method of controlling undesirable vegetation comprising contacting the vegetation or applying to the soil or water adjacent thereto with a safened herbicidal composition comprising a herbicidally effective amount of (a) the benzyl ester of the compound of formula (I)

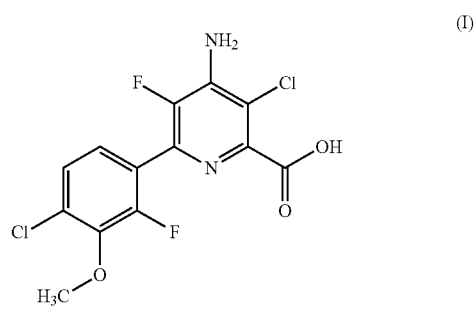 [SMILES: COc1c(Cl)ccc(-c2nc(C(=O)O)c(Cl)c(N)c2F)c1F]

and (b) a safener.

11. The method of claim 10, wherein the undesirable vegetation is controlled in wheat and barley.

12. The method of claim 10, wherein the safener is from the quinolinyloxyacetate family of chemicals.

13. The method of claim 12, wherein the safener is cloquintocet acid, cloquintocet mexyl, cloquintocet triisopropylamine, or cloquintocet dimethylamine.

14. The method of claim 13, wherein the safener is cloquintocet mexyl.

15. The method of claim 10, wherein (a) is an agriculturally acceptable benzyl ester of the compound of formula (I) and (b) is cloquintocet mexyl.

16. The method of claim 10, wherein the weight ratio of (a) to (b) is from 64:1 to 1:32.

17. The method of claim 10, wherein the weight ratio of (a) to (b) is from 2:1 to 1:2.

18. The method of claim 10, further comprising an agriculturally acceptable adjuvant or carrier.

19. The method of claim 10, wherein the undesirable vegetation is controlled in glyphosate, glufosinate, dicamba, phenoxy auxins, pyridyloxy auxins, aryloxyphenoxypropionates, acetyl CoA carboxylase (ACCase) inhibitors, imidazolinones, acetolactate synthase (ALS) inhibitors, 4-hydroxyphenyl-pyruvate dioxygenase (HPPD) inhibitors, protoporphyrinogen oxidase (PPO) inhibitors, triazines, and bromoxynil tolerant crops possessing multiple or stacked traits conferring tolerance to multiple chemistries and/or multiple modes of action.

* * * * *